US00PP31961P2

(12) United States Plant Patent
van Geest

(10) Patent No.: US PP31,961 P2
(45) Date of Patent: Jul. 14, 2020

(54) ***FICUS* PLANT NAMED 'ESPE1702'**

(50) Latin Name: *Ficus benjamina*
Varietal Denomination: ESPE1702

(71) Applicant: J. Van Geest Holding B.V., Gravenzande (NL)

(72) Inventor: Jan van Geest, Gravenzande (NL)

(73) Assignee: J. Van Geest Holding B.V., Gravenzande (NL)

( * ) Notice: Subject to any disclaimer, the term of this patent is extended or adjusted under 35 U.S.C. 154(b) by 0 days.

(21) Appl. No.: 16/501,280

(22) Filed: Mar. 16, 2019

(51) Int. Cl.
*A01H 5/00* (2018.01)
*A01H 6/00* (2018.01)

(52) U.S. Cl.
USPC ..... Plt./211

(58) Field of Classification Search
USPC ..... Plt./211
CPC ... A01H 5/00; A01H 5/08; A01H 5/12; A01H 6/00
See application file for complete search history.

(56) References Cited

PUBLICATIONS

Upov Pluto Plant Variety Database Nov. 18, 2019 [retrieved on Nov. 18, 2019] [online], retrieved from the Internet at https://www.upov.int/pluto/en/index.jsp, one page. (Year: 2019).*

* cited by examiner

*Primary Examiner* — June Hwu
(74) *Attorney, Agent, or Firm* — Samuel R. McCoy, Jr.

(57) ABSTRACT

A new and distinct variety of *Ficus* plant named 'ESPE1702' which is characterized by an abundance of narrow ovate to oblong foliage on a relatively compact plant, foliage with an aristate to caudate leaf apex, foliage which varies in color from light green to dark green, and the stability of all characteristics from generation to generation.

2 Drawing Sheets

Latin name of the genus and species: The Latin name of the genus and species of the novel variety disclosed herein is *Ficus benjamina.*

Variety denomination: The inventive variety of *Ficus* disclosed herein has been given the variety denomination 'ESPE1702'.

BACKGROUND OF THE INVENTION

Parentage: 'ESPE1702' originated as a naturally occurring, whole-plant mutation of *Ficus benjamina* 'Danielle' (Community Plant Variety Rights grant number 590). In the summer of 2015, the inventor discovered the mutation at his commercial greenhouse in Gravenzande, The Netherlands, growing amongst a cultivated population of 'Danielle' plants. The mutation was noted for its compact habit and relative abundance of foliage ranging in color from light to dark green and was subsequently isolated for further evaluation in order to confirm the distinctness and stability of the characteristics first observed. Upon confirmation of distinctness and stability, 'ESPE1702' was selected for commercialization.

Asexual Reproduction: Asexual reproduction of 'ESPE1702', by way of stem cuttings, was first initiated in the summer of 2015 at a commercial greenhouse in Gravenzande, The Netherlands. Through five subsequent generations, the unique features of this cultivar have proven to be stable and true to type.

SUMMARY OF THE INVENTION

The cultivar 'ESPE1702' has not been observed under all possible environmental conditions and the phenotype may vary somewhat with variations in environment such as temperature, day length, and light intensity, without, however, any variance in genotype. The following traits have been repeatedly observed and are determined to be the unique characteristics of 'ESPE1702'. These characteristics in combination distinguish 'ESPE1702' as a new and distinct *Ficus* cultivar:

1. *Ficus* 'ESPE1702' exhibits an abundance of narrow ovate to oblong foliage on a relatively compact plant; and
2. *Ficus* 'ESPE1702' exhibits foliage with an aristate to caudate leaf apex; and
3. *Ficus* 'ESPE1702' exhibits foliage with a somewhat relaxed attitude; and
4. *Ficus* 'ESPE1702' exhibits foliage which varies in color from light green to dark green.

BOTANICAL DESCRIPTION OF THE PLANT

Figure 1:
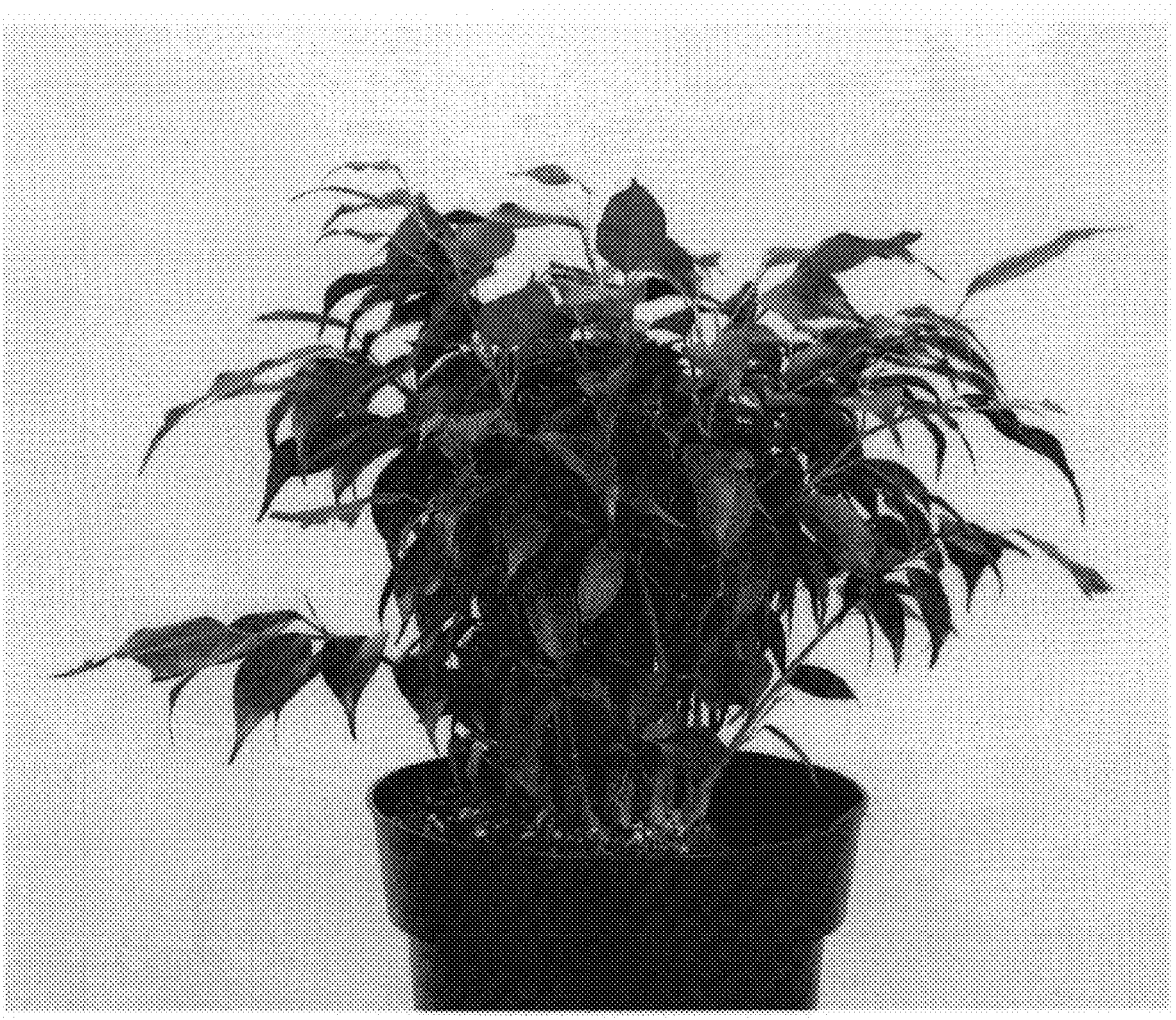
FIG. 1 illustrates, as nearly true as it is reasonably possible to make the same in color photographs of this type, an exemplary plant of 'ESPE1702' grown in a commercial greenhouse in Gravenzande, The Netherlands. This plant is approximately 26 weeks old, shown planted in a 15 cm container.
Figure 2:
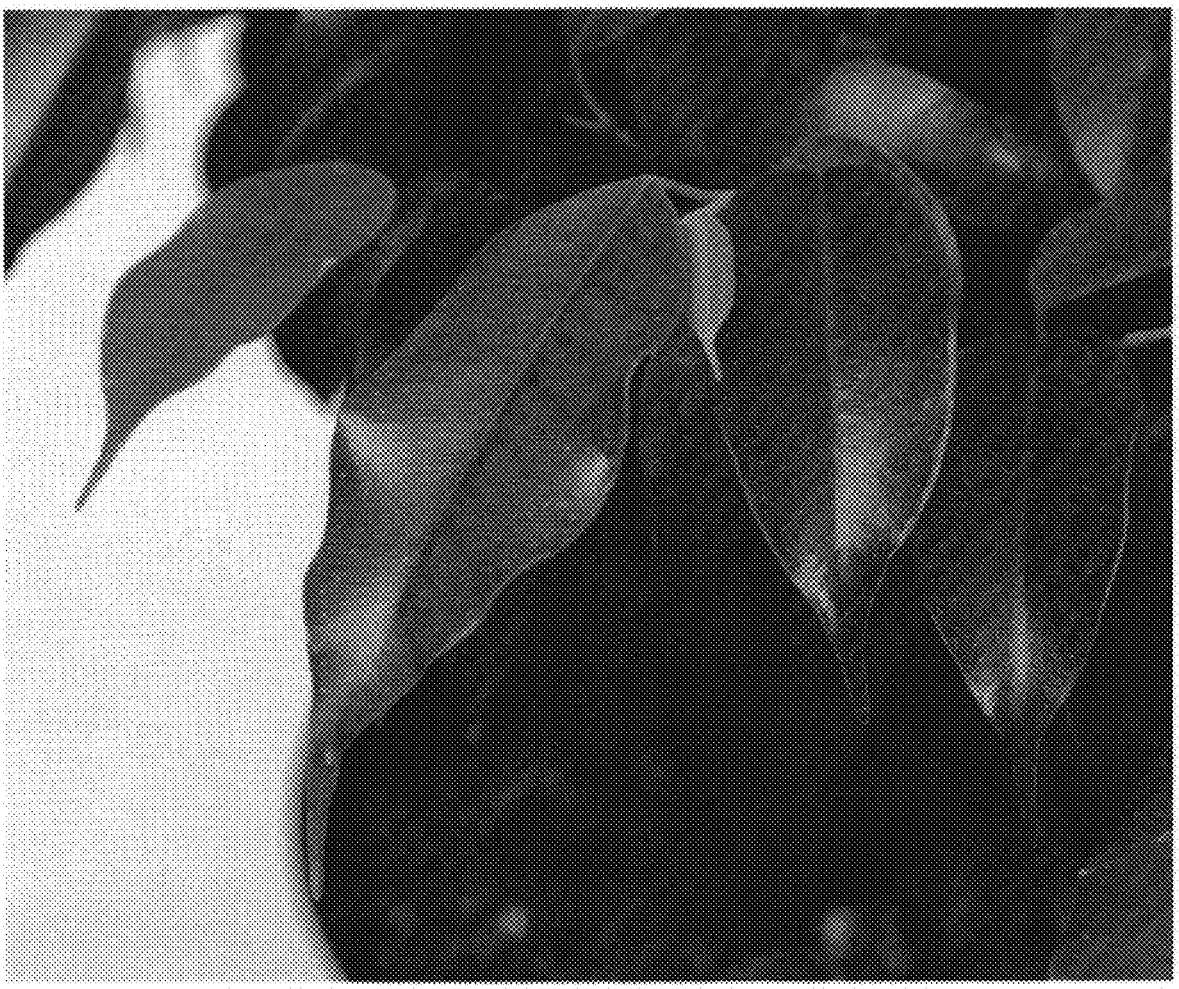
FIG. 2 illustrates, as nearly true as it is reasonably possible to make the same in color photographs of this type, the typical foliage of 'ESPE1702'.

The following observations and measurements were made in February of 2019 and describe a sample set of six 26 week-old 'ESPE1702' plants grown in 15 cm nursery pots at a greenhouse in Gravenzande, The Netherlands. Plants were produced in a greenhouse with full sun exposure, ebb and flood irrigation tables, no supplemental fertilizer, and no preventative or pest control measures utilized.

Those skilled in the art will appreciate that certain characteristics will vary with older or, conversely, with younger plants. 'ESPE1702' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climactic and cultural conditions. Color notations are based on *The Royal Horticultural Society Colour Chart*, The Royal Horticultural Society, London, 2015 (sixth edition).

A botanical description of 'ESPE1702' and comparisons with the parent plant and most similar commercial variety of *Ficus* are provided below.

Plant description:

*Growth habit*.—Broad, upright to spreading broadleaf evergreen.

*Plant form*.—Globular to broad obovate.

*Average height*.—23.3 cm from the soil level to the top of the foliar plane.

*Plant spread*.—Average of 35.1 cm.

*Growth rate*.—Slow.

*Plant vigor*.—Moderately vigorous.

*Propagation type*.—Stem cuttings.

*Time to produce a rooted cutting*.—Approximately 40 days to produce a rooted cutting at approximately 25 degrees Celsius.

*Time to produce a finished plant*.—Approximately 15 weeks to produce a marketable finished plant in a 14 cm pot.

*Disease resistance*.—Neither resistance nor susceptibility to typical *Ficus benjamina* pests and diseases has been observed.

*Environmental tolerances*.—Adapt to, at least, USDA Zones 10 through 13 and temperatures as high as 40 degrees Celsius; moderate to high tolerance to rain; moderate tolerance to wind.

Root system:

*General*.—Moderately dense, moderately branched rooting; roots are slightly fibrous.

*Distribution in the soil profile*.—Shallow to moderately deep.

*Diameter of roots*.—0.75 mm on average.

*Texture*.—Smooth; no root hairs.

*Color*.—Greyed-orange, nearest to a combination of RHS 164A and 164B.

Stem:

*General branching habit*.—Basally branching main stems; with lateral branching. Stems produce a milky exudate when damaged.

*Main stem*.—Quantity — 16. Attitude — Upright. Aspect — Rounded. Strength — Strong. Color, immature stems — Yellow-green, nearest to RHS 144B. Color, mature stems — Yellow-green, nearest to a mixture of RHS 148A and 148B. Color at internodes — Yellow-green, nearest to a mixture of RHS 148A and 148B. Color, oldest wood — Greyed-brown, nearest to a combination of RHS 199A and N199A. Texture — Glabrous with small elliptical lenticels with an average length of 0.5 mm and a width of 0.2 mm. Luster — Slightly glossy.

*Lateral branches*.—Quantity — 40. Length — 8.4 cm. Diameter — 2.0 cm. Internode length — 1.3 cm. Attitude — Outward; at an approximate angle of 40 degrees to the main stems. Shoot tips are semi-erect. Aspect — Rounded. Strength — Moderately strong. Texture — Glabrous with small elliptical lenticels with an average length of 0.5 mm and a width of 0.2 mm. Luster — Slightly glossy. Color, immature stems — Yellow-green, nearest to RHS 144B. Color, mature stems — Yellow-green, nearest to a mixture of RHS 148A and 148B. Color at internodes — Yellow-green, nearest to a mixture of RHS 148A and 148B.

Foliage:

*Arrangement*.—Alternate.

*Division*.—Simple.

*Quantity*.—7 leaves per lateral branch.

*Attitude*.—At an average angle of 40 degrees to the branch.

*Lamina*.—Shape — Narrowly ovate to oblong; leaf tip is short relative to the total length of the lamina. Aspect — Slightly carinate to flat, with the distal portion curled downward. Dimensions — 5.7 cm long and 2.3 cm wide. Apex — Aristate to caudate. Base — Acute to near obtuse. Margin — Entire; coarsely undulate. Texture and luster of the adaxial surface — Glabrous and moderately glossy, with small orbicular glands visible along the margins; glands are approximately 0.2 mm in diameter and are colored yellow-green, nearest to RHS 150C. Texture and luster of the abaxial surface — Smooth, glabrous, and very slightly glossy. Color — Juvenile foliage, adaxial surface — Yellow-green, nearest to RHS 144A. Juvenile foliage, abaxial surface — Yellow-green, nearest to RHS 144A. Mature foliage, adaxial surface — Nearest to in between yellow-green, RHS 147A, and greyed-green, RHS N189A. Mature foliage, abaxial surface — Nearest to in between green, RHS 137B, and yellow-green, RHS 147B. Venation — Pattern — Pinnate. Color, adaxial surface — Green, nearest to RHS NN137C. Color, abaxial surface — Yellow-green, nearest to a mixture of RHS 145B and 145C.

*Stipule*.—Not present.

*Petiole*.—Length — 0.9 cm. Diameter — 0.1 cm. Strength — Strong. Texture — Smooth; glabrous. Luster — Very slightly glossy. Color, adaxial surface — Yellow-green, nearest to RHS 146C. Color, abaxial surface — Yellow-green, nearest to RHS 146C.

Inflorescence: No flowering has been observed to date.

COMPARISON WITH THE PARENT PLANT

Plants of the new cultivar 'ESPE1702' differ from the parent, *Ficus benjamina* 'Danielle' (Community Plant Variety Rights grant number 590), in the following characteristics described in Table 1 below.

TABLE 1

| Characteristic | 'ESPE1702' | 'Danielle' |
|---|---|---|
| Foliage shape. | Narrow ovate to oblong. | Broad ovate. |
| Foliage apex. | Aristate to caudate. | Acuminate to caudate. |
| General coloration of the mature foliage. | Lighter green. | Darker green. |

COMPARISON WITH THE CLOSEST KNOWN COMPARATOR

Plants of the new cultivar 'ESPE1702' differs from the variety, *Ficus* sp. 'ESPE1703' (U.S. patent application Ser. No. 16/501,276), for which a United States plant patent application is being filed concurrently with the instant application, in the following characteristics described in Table 2 below.

TABLE 2

| Characteristic | 'ESPE1702' | 'ESPE1703' |
|---|---|---|
| General plant profile. | Slightly taller and narrower than 'ESPE1703'. | Shorter and wider than 'ESPE1702'. |
| Abundance of foliages | More abundant. | Less abundant. |
| Foliage attitude. | More upright. | More relaxed. |
| General coloration of the foliage. | Green. | Green and blotched yellow-green; irregularly and broadly margined yellow to green-white. |

That which is claimed is:

1. A new and distinct variety of *Ficus* plant named 'ESPE1702', substantially as described and illustrated herein.

* * * * *